US010703781B2

(12) United States Patent
Nilsen et al.

(10) Patent No.: US 10,703,781 B2
(45) **Date of Patent: *Jul. 7, 2020**

(54) PISCINE MYOCARDITIS VIRUS-LIKE PARTICLES AND METHODS OF USE THEREOF

(71) Applicant: PHARMAQ AS, Overhalla (NO)

(72) Inventors: Pal Nilsen, Overhalla (NO); Marit Rode, Overhalla (NO)

(73) Assignee: PHARMAQ AS, Overhalla (NO)

(*) Notice: Subject to any disclaimer, the term of this patent is extended or adjusted under 35 U.S.C. 154(b) by 0 days.

This patent is subject to a terminal disclaimer.

(21) Appl. No.: 16/544,060

(22) Filed: Aug. 19, 2019

(65) Prior Publication Data

US 2020/0002385 A1 Jan. 2, 2020

Related U.S. Application Data

(63) Continuation of application No. 15/883,202, filed on Jan. 30, 2018, now Pat. No. 10,428,117.

(51) Int. Cl.

| | |
|---|---|
| *C07K 14/005* | (2006.01) |
| *C12N 15/85* | (2006.01) |
| *A61K 39/12* | (2006.01) |
| *C12N 7/00* | (2006.01) |
| *A61K 39/00* | (2006.01) |

(52) U.S. Cl.

CPC ............ *C07K 14/005* (2013.01); *A61K 39/12* (2013.01); *C12N 7/00* (2013.01); *C12N 15/85* (2013.01); *A61K 2039/5258* (2013.01); *A61K 2039/552* (2013.01); *C12N 2710/14143* (2013.01); *C12N 2720/00022* (2013.01); *C12N 2720/00023* (2013.01); *C12N 2720/00034* (2013.01); *C12N 2720/00051* (2013.01); *C12N 2720/00071* (2013.01)

(58) Field of Classification Search

None

See application file for complete search history.

(56) References Cited

U.S. PATENT DOCUMENTS 10,428,117 B2 * 10/2019 Nilsen .................... C12N 15/85

FOREIGN PATENT DOCUMENTS

WO WO 2011/131600 A1 10/2011

OTHER PUBLICATIONS

Shivappa, R. B. et al., 2005, "Development of a Subunit Vaccine for Infectious Pancreatic Necrosis Virus Using a Baculovirus Insect/Larvae System," Dev. Biol. Basel, Karger, vol. 121, pp. 165-174.

Metz, S. W. et al., 2011, "Low Temperature-Dependent Salmonid Alphavirus Glycoprotein Processing and Recombinant Virus-Like Particle Formation," PLOS One, vol. 6, e25816.

Wiik-Nielsen et al., 2013, "Genetic variation in Norwegian piscine myocarditis virus in atlantic salmon, *Salmo salar* L.," Journal of Fish Diseases, vol. 36, pp. 129-139.

Haugland, O. et al., 2011, "Cardiomyopathy Syndrome of Atlantic Salmon (*Salmo salar* L.) is Caused by a Double-Stranded RNA Virus of the Totiviridae Family," Journal of Virology, vol. 85, pp. 5275-5286.

Dhar, A. K. et al., 2014, "Viral vaccines for farmed finfish," Virus Disease, vol. 25, pp. 1-17.

Garseth, A. H. et al., 2018, "Cardiomyopathy syndrome in Atlantic salmon *Salmo salar* L.: A review of the current state of knowledge," Journal of Fish Disease, vol. 41, pp. 11-26.

PCT International Search Report and Written Opinion, International Application No. PCT/US2018/015824, International filed Jan. 30, 2018, dated Apr. 9, 2018.

Somasundaram, B. et al., 2016, "Characterizing Enterovirus 71 and Coxsackievirus A16 virus-like particles production in insect cells," Methods, vol. 95, pp. 38-45.

Patel, M. C. et al., 2009, "Production of immunogenic human papillomavirus-16 major capsid protein derived virus like particles," Indian Journal of Med. Res., vol. 130, pp. 213-218.

UK Search and Examination Report, Application No. GB1701573.6, dated Nov. 29-30, 2017.

Dunn et al. (PLoS Mar. 2013; 9 (3): e1003225).

Sequence alignment of SEQ ID No. 2 with Geneseq database access No. AZ009846 in WO 2011/131600 on Oct. 2011.

* cited by examiner

*Primary Examiner* — Shanon A. Foley

(74) *Attorney, Agent, or Firm* — Vyacheslav Vasilyev

(57) ABSTRACT

The present invention relates to a piscine myocarditis virus (PMCV) virus-like particle (VLP) which consists only of PMCV ORF1 protein.

14 Claims, 4 Drawing Sheets

Specification includes a Sequence Listing.

```
 327                                             ....ATGG AACCAAACAC ATCTGTCATT
 351 GCAACGGAGC AGCAGCAGGC TGCCATGAGA GAGGTGGAGG CCGAGGCGGC
 401 GGCCAGAGAC GAAGTGGTGG AGAAGATCGC ATTCGCTGAA GGAGCGATGA
 451 TGGTACAGAC GAGGAGGTTA CCATCAGGAA AGTCGTCGGT AGGAGGTTTT
 501 CTCGGCGAAC TGGCACAGAA CATACGTGCC ATGAATCGGT CATTGCACAC
 551 AGATACCAAC ATGCTGACCG AAGGGGCGAT GGTGGACAGA GCGAGGGCAA
 601 AAGTACACAA AATCATTAGG GAAGGGAATT TGGACTCTAG GGTATTTTCA
 651 AACACGGGGA GCAACACTAT GTTGTCACTG TGGGTACCAG CAGTACCGGG
 701 ACCACCGGCA GTACCGGAGC ATTGGGACGT TGCGCCGTCC TGGTTCGTAT
 751 GCAGACCGGG GAAAAAGGGG GGGATAAAGA TCACACAAAG CGCATCAATG
 801 GCAGCATTAA ACCCACTATT TAGAGGCGCA GACGTGGGGC CAATCGGGAC
 851 AGCAGTCAGG GCGGATGTAA ACGCATTTTC AATGAATGCA GTTCTGGGAG
 901 CACTAAGAGC CGGGGGATTT AACACCGAAC ATTCCCTGGT GTCATTCGTT
 951 GAACCACTAA TTCGGATCTT GCTAATGGGG GTACAAACAC AAGACAGGGG
1001 GACCAGCCCA TGGGATTGGG TTGGAGGGAT GAGTTCGCGA ATAGTCAATC
1051 CCCTAGTATT CACAACAAGC GGGAACTTCT TCCCAGGGGG ACCAAATTTG
1101 AGGGTGTGGG GAGCCAACGA TACAGTGGCC AGGATAGTAA ACGTTGAGGA
1151 CTACATGCGC GAGGCGGCCG GGGAGGGGAG GTTCGACGCT GGATGGGGAC
1201 CGGAATTCTG GGGTGGGACA GGGGACGACG CAGTGGCGGT GGTACCGATA
1251 AGGGCAGTAG AAGCAGGGCT AGGAGAAGTA AACGCAGGGT GGACATTGGC
1301 ACACATGAAA TACCCAGTCA AGGTTAGACT ACTTGACGTC GACGACCGAA
1351 CAATTGGACC AGGGGGGAGC CTGCCCCTAA ACGCAAACAG AGAATACACG
1401 GCGGCAGGAG CTACGCATGT ACCCGGGCCC TATGCCAGGG TACTGTACGT
1451 CGTCGTGGAC CAAAACGCAG ACAGGTGTGT GGGGGTGAGA GTGCAGGGAC
1501 AGGGTGCTGT AATTGACGTG GATCCGGCGT TGAATTACGT GATAGGGGGA
1551 GCGGATTTGG GGATGTTGCC GTTGATACAG TGGAGTGTAG GGCTGGGGGC
1601 CGAGGACATG GCGCAGGGAT CGATTGCACA GACGCAGCGA TGGGTGAGGA
1651 TGTATGGAAA CGAGGACGAT TGGGAATCAG CGTGGCATCT AGTGTCTAGC
1701 GCGTACACAG TGTACAGCCC GGCATTCAGG AGATCGGGTG TCGCAGTGGA
1751 GGGAGGATTC TGGGCGCAAC CAGCTGCAGG GGCAGCACCG TTTCCACTAG
1801 GAGGATTGGC AGGGTGGGTG AGGTACGACA ATCAGGCACG GGCGGCGCAG
1851 GTTGCACTTT GCAGAGAGAG GGCGGATATG GCGGAGTGTC CTTGGGGGGG
1901 GTACAGGGAG AGAGGGGTGA GACCGGGGAG TGTGGCAAAC TGGCAGTACG
1951 TAAGGTTCGA TCCCACAGTG GCTGTAGGAG TAGCTGCTCA CTTCTGGTCG
2001 GTAGTGAAGG TGATGGTGGC TCCCGTCCCA GACAGAGCGG CTGCTCTGGC
2051 GGACATGGCG TGGGGGAAGG GGAAGGTGCA AGCCATGGGT GAGGATGTGA
2101 TCAACGGGCA GATGGGACAA CCTGAGTCCA TGATGAGAGG GGTGGCGCTG
2151 AACGAGAACC AGGGACTAGC GGCGGCTACA GTCAGGAGGG TGGTTGGGCT
2201 GGAGAACGAG TCGATGCAAA CAACGCACTG GAGTACAACG GAGGTAGCAA
2251 TGAACGGGTA CTACGGGAGA GCAGGAGCAA CAGCACACCA CGCTGCATTT
2301 CCGTTGTCCG AGGGGGGGAC AATGCGAAAA CGAATACCAG CTATAGAGAT
2351 GAGGGAGAAC GGGGTGGAGG GGGACCTGAT GAACGATGAT CTCTATTCAA
2401 TTGGAACGGC AGCGGGGTAC CTGGCGGTAG AGGGGATGGC AGGTGCGCAG
2451 GGGGGTATCT GGGACGTGGT CCAGTACCAG CTGCCTGGGC CTGACGATGA
2501 GGCGAGGGGG GTGATGAACA CGGTGGGGGC GATGGGGGGA TGGACGAGGG
2551 CGGTGACACC AGTAGACAAT GTGGCCACCA TGAGGGACAA CGGGGTTGAG
2601 GGGGAACCTT GTGGAATAGT GATGTCTCTA CCAACAAGTG GGACCGCTGT
2651 GGTGGATAGG TTAGCTAATT TCGGATTACC ACCAGCGAGG GCGGAATTAA
2701 GAGAAGTACC ATTTGGCGGG TACCAAAGAT CAGTCACAAA CACCAACCAC
2751 AGAGTCAAGG TGAGTGTGAG TGGGGGGCGA GCAGTTGTTC AAAAAGGGAA
2801 CAAAGCCGAG ATGAATCCAG TCTTTGTCAA TAGGACACCA GGACAAACGA
2851 CCCTAGGCCA ACCAACAACA GACACTACAG GGATGACAAC TGCAGATTTT
2901 TTAGATATAT AG    (SEQ ID NO.1)
```

FIG. 1

```
MEPNTSVIATEQQQAAMREVEAEAAARDEVVEKIAFAEGAMMVQTRRLPS   50
GKSSVGGFLGELAQNIRAMNRSLHTDTNMLTEGAMVDRARAKVHKIIREG  100
NLDSRVFSNTGSNTMLSLWVPAVGPPAVPEHWDVAPSWFVCRPGKKGGI   150
KITQSASMAALNPLFRGADVGPIGTAVRADVNAFSMNAVLGALRAGGFNT  200
EHSLVSFVEPLIRILLMGVQTDRGTSPWDWVGGMSSRIVNPLVFTTSGN   250
FFPGGPNLRVWGANDTVARIVNVEDYMREAAGEGRFDAGWGPEFWGGTGD  300
DAVAVVPIRAVEAGLGEVNAGWTLAHMEYPVKVRLLDVDDRTIGPGGSLP  350
LNANREYTAAGATHVPGPYARVLYVVVDQNADRCVGVRVQGQGAVIDVDP  400
ALNYVIGGADLGMLPLIQWSVGLGAEDMAQGSIAQTQRWVRMYGNEDDWE  450
SAWHLVSSAYTVYSPAFRRSGVAVEGGFWAQPAAGAAPFPLGGLAGWVRY  500
DNQARAAQVALCRERADMAECPWGGYRERGVRPGSVANWQYVRFDPTVAV  550
GVAAHFWSVVKVMVAPVPDRAAALADMAWGKGKVQAMGEDVINGQMGQPE  600
SMMRGVALNENQGLAAATVRRVVGLENESMQTTHWSTTEVAMNGYYGRAG  650
ATAHHAAFPLSEGGTMRKRIPAIEMRENGVEGDLMNDDLYSIGTAAGYLA  700
VEGMAGAQGGIWDVVQYQLPGPDDEARGVMNTVGAMGGWTRAVTPVDNVA  750
TMRDNGVEGEPCGIVMSLPTSGTAVVDRLANFGLPPARAELREVPFGGYQ  800
RSVTNTNHRVKVSVSGGRAVVQKGNKAEMNPVFVNRTPGQTTLGQPTTDT  850
TGMTTADFLDI*    (SEQ ID NO.2)
```

FIG. 2

SEQUENCE LISTING

<160> NUMBER OF SEQ ID NOS: 2

<210> SEQ ID NO 1
<211> LENGTH: 2586
<212> TYPE: DNA
<213> ORGANISM: Piscine Myocarditis Virus

<400> SEQUENCE: 1

```
atggaaccaa acacatctgt cattgcaacg gagcagcagc aggctgccat gagagaggtg      60
gaggccgagg cggcggccag agacgaagtg gtggagaaga tcgcattcgc tgaaggagcg     120
atgatggtac agacgaggag gttaccatca ggaaagtcgt cggtaggagg tttctcggc      180 gaactggcac agaacatacg tgccatgaat cggtcattgc acacagatac caacatgctg     240
accgaagggg cgatggtgga cagagcgagg gcaaaagtac acaaaatcat tagggaaggg     300
aatttggact ctagggtatt ttcaaacacg gggagcaaca ctatgttgtc actgtgggta     360
ccagcagtac cgggaccacc ggcagtaccg gagcattggg acgttgcgcc gtcctggttc     420
gtatgcagac cggggaaaaa gggggggata aagatcacac aaagcgcatc aatggcagca     480
ttaaacccac tatttagagg cgcagacgtg gggccaatcg gacagcagt cagggcggat      540 gtaaacgcat tttcaatgaa tgcagttctg ggagcactaa gagccggggg atttaacacc     600
gaacattccc tggtgtcatt cgttgaacca ctaattcgga tcttgctaat gggggtacaa     660
acacaagaca gggggaccag cccatgggat tgggttggag ggatgagttc gcgaatagtc     720
aatcccctag tattcacaac aagcgggaac ttcttcccag ggggaccaaa tttgagggtg     780
tggggagcca acgatacagt ggccaggata gtaaacgttg aggactacat gcgcgaggcg     840
gccggggagg ggaggttcga cgctggatgg ggaccggaat tctggggtgg gacaggggac     900
gacgcagtgg cggtggtacc gataagggca gtagaagcag ggctaggaga agtaaacgca     960
gggtggacat tggcacacat ggaataccca gtcaaggtta gactacttga cgtcgacgac    1020
cgaacaattg gaccaggggg gagcctgccc ctaaacgcaa acagagaata cacggcggca    1080
ggagctacgc atgtacccgg gccctatgcc agggtactgt acgtcgtcgt ggaccaaaac    1140
gcagacaggt gtgtgggggt gagagtgcag ggacagggtg ctgtaattga cgtggatccg    1200
gcgttgaatt acgtgatagg gggagcggat ttggggatgt tgccgttgat acagtggagt    1260
gtagggctgg gggccgagga catggcgcag ggatcgattg cacagacgca gcgatggggta   1320 aggatgtatg gaaacgagga cgattgggaa tcagcgtggc atctagtgtc tagcgcgtac    1380
```

-continued

```
acagtgtaca gcccggcatt caggagatcg ggtgtcgcag tggagggagg attctgggcg    1440
caaccagctg caggggcagc accgttccca ctaggaggat tggcagggtg ggtgaggtac    1500
gacaatcagg cacgggcggc gcaggttgca ctttgcagag agagggcgga tatggcggag    1560
tgtccttggg gggggtacag ggagagaggg gtgagaccgg ggagtgtggc aaactggcag    1620
tacgtaaggt tcgatcccac agtggctgta ggagtagctg ctcacttctg gtcggtagtg    1680
aaggtgatgg tggctcccgt cccagacaga gcggctgctc tggcggacat ggcgtggggg    1740
aaggggaagg tgcaagccat gggtgaggat gtgatcaacg ggcagatggg acaacctgag    1800
tccatgatga gagggtggc gctgaacgag aaccagggac tagcggcggc tacagtcagg    1860
agggtggttg ggctggagaa cgagtcgatg caaacaacgc actggagtac aacggaggta    1920
gcaatgaacg ggtactacgg gagagcagga gcaacagcac accacgctgc atttccgttg    1980
tccgaggggg ggacaatgcg aaaacgaata ccagctatag agatgaggga gaacggggtg    2040
gagggggacc tgatgaacga tgatctctat tcaattggaa cggcagcggg gtacctggcg    2100
gtagagggga tggcaggtgc gcagggggt atctgggacg tggtccagta ccagctgcct    2160
gggcctgacg atgaggcgag gggggtgatg aacacggtgg gggcgatggg gggatggacg    2220
agggcggtga caccagtaga caatgtggcc accatgaggg acaacggggt tgaggggaa    2280 ccttgtggaa tagtgatgtc tctaccaaca agtgggaccg ctgtggtgga taggttagct    2340
aatttcggat taccaccagc gagggcgaaa ttaagaaag taccatttgg cgggtaccaa    2400
agatcagtca caaacaccaa ccacagagtc aaggtgagtg tgagtggggg gcgagcagtt    2460
gttcaaaaag gaacaaagc cgagatgaat ccagtctttg tcaataggac accaggacaa    2520
acgaccctag gccaaccaac aacagacact acagggatga caactgcaga ttttttagat    2580
atatag                                                               2586
```

<210> SEQ ID NO 2
<211> LENGTH: 861
<212> TYPE: PRT
<213> ORGANISM: Piscine Myocarditis Virus

<400> SEQUENCE: 2

```
Met Glu Pro Asn Thr Ser Val Ile Ala Thr Glu Gln Gln Gln Ala Ala
1               5                   10                  15

Met Arg Glu Val Glu Ala Glu Ala Ala Arg Asp Glu Val Val Glu
            20                  25                  30

Lys Ile Ala Phe Ala Glu Gly Ala Met Met Val Gln Thr Arg Arg Leu
        35                  40                  45

Pro Ser Gly Lys Ser Ser Val Gly Gly Phe Leu Gly Glu Leu Ala Gln
    50                  55                  60

Asn Ile Arg Ala Met Asn Arg Ser Leu His Thr Asp Thr Asn Met Leu
65                  70                  75                  80

Thr Glu Gly Ala Met Val Asp Arg Ala Arg Ala Lys Val His Lys Ile
                85                  90                  95

Ile Arg Glu Gly Asn Leu Asp Ser Arg Val Phe Ser Asn Thr Gly Ser
            100                 105                 110

Asn Thr Met Leu Ser Leu Trp Val Pro Ala Val Pro Gly Pro Pro Ala
        115                 120                 125

Val Pro Glu His Trp Asp Val Ala Pro Ser Trp Phe Val Cys Arg Pro
    130                 135                 140

Gly Lys Lys Gly Gly Ile Lys Ile Thr Gln Ser Ala Ser Met Ala Ala
145                 150                 155                 160
```

-continued

```
Leu Asn Pro Leu Phe Arg Gly Ala Asp Val Gly Pro Ile Gly Thr Ala
                165                 170                 175

Val Arg Ala Asp Val Asn Ala Phe Ser Met Asn Ala Val Leu Gly Ala
            180                 185                 190

Leu Arg Ala Gly Gly Phe Asn Thr Glu His Ser Leu Val Ser Phe Val
        195                 200                 205

Glu Pro Leu Ile Arg Ile Leu Leu Met Gly Val Gln Thr Gln Asp Arg
    210                 215                 220

Gly Thr Ser Pro Trp Asp Trp Val Gly Gly Met Ser Ser Arg Ile Val
225                 230                 235                 240

Asn Pro Leu Val Phe Thr Thr Ser Gly Asn Phe Phe Pro Gly Gly Pro
                245                 250                 255

Asn Leu Arg Val Trp Gly Ala Asn Asp Thr Val Ala Arg Ile Val Asn
            260                 265                 270

Val Glu Asp Tyr Met Arg Glu Ala Ala Gly Glu Gly Arg Phe Asp Ala
        275                 280                 285

Gly Trp Gly Pro Glu Phe Trp Gly Gly Thr Gly Asp Asp Ala Val Ala
    290                 295                 300

Val Val Pro Ile Arg Ala Val Glu Ala Gly Leu Gly Glu Val Asn Ala
305                 310                 315                 320

Gly Trp Thr Leu Ala His Met Glu Tyr Pro Val Lys Val Arg Leu Leu
                325                 330                 335

Asp Val Asp Asp Arg Thr Ile Gly Pro Gly Gly Ser Leu Pro Leu Asn
            340                 345                 350

Ala Asn Arg Glu Tyr Thr Ala Ala Gly Ala Thr His Val Pro Gly Pro
        355                 360                 365

Tyr Ala Arg Val Leu Tyr Val Val Asp Gln Asn Ala Asp Arg Cys
    370                 375                 380

Val Gly Val Arg Val Gln Gly Gln Gly Ala Val Ile Asp Val Asp Pro
385                 390                 395                 400

Ala Leu Asn Tyr Val Ile Gly Gly Ala Asp Leu Gly Met Leu Pro Leu
                405                 410                 415

Ile Gln Trp Ser Val Gly Leu Gly Ala Glu Asp Met Ala Gln Gly Ser
            420                 425                 430

Ile Ala Gln Thr Gln Arg Trp Val Arg Met Tyr Gly Asn Glu Asp Asp
        435                 440                 445

Trp Glu Ser Ala Trp His Leu Val Ser Ser Ala Tyr Thr Val Tyr Ser
    450                 455                 460

Pro Ala Phe Arg Arg Ser Gly Val Ala Val Glu Gly Gly Phe Trp Ala
465                 470                 475                 480

Gln Pro Ala Ala Gly Ala Ala Pro Phe Pro Leu Gly Gly Leu Ala Gly
                485                 490                 495

Trp Val Arg Tyr Asp Asn Gln Ala Arg Ala Ala Gln Val Ala Leu Cys
            500                 505                 510

Arg Glu Arg Ala Asp Met Ala Glu Cys Pro Trp Gly Gly Tyr Arg Glu
        515                 520                 525

Arg Gly Val Arg Pro Gly Ser Val Ala Asn Trp Gln Tyr Val Arg Phe
    530                 535                 540

Asp Pro Thr Val Ala Val Gly Val Ala Ala His Phe Trp Ser Val Val
545                 550                 555                 560

Lys Val Met Val Ala Pro Val Pro Asp Arg Ala Ala Leu Ala Asp
                565                 570                 575
```

```
Met Ala Trp Gly Lys Gly Lys Val Gln Ala Met Gly Glu Asp Val Ile
            580                 585                 590
Asn Gly Gln Met Gly Gln Pro Glu Ser Met Met Arg Gly Val Ala Leu
        595                 600                 605
Asn Glu Asn Gln Gly Leu Ala Ala Ala Thr Val Arg Arg Val Val Gly
    610                 615                 620
Leu Glu Asn Glu Ser Met Gln Thr Thr His Trp Ser Thr Thr Glu Val
625                 630                 635                 640
Ala Met Asn Gly Tyr Tyr Gly Arg Ala Gly Ala Thr Ala His His Ala
            645                 650                 655
Ala Phe Pro Leu Ser Glu Gly Gly Thr Met Arg Lys Arg Ile Pro Ala
            660                 665                 670
Ile Glu Met Arg Glu Asn Gly Val Glu Gly Asp Leu Met Asn Asp Asp
            675                 680                 685
Leu Tyr Ser Ile Gly Thr Ala Ala Gly Tyr Leu Ala Val Glu Gly Met
690                 695                 700
Ala Gly Ala Gln Gly Gly Ile Trp Asp Val Val Gln Tyr Gln Leu Pro
705                 710                 715                 720
Gly Pro Asp Asp Glu Ala Arg Gly Val Met Asn Thr Val Gly Ala Met
            725                 730                 735
Gly Gly Trp Thr Arg Ala Val Thr Pro Val Asp Asn Val Ala Thr Met
            740                 745                 750
Arg Asp Asn Gly Val Glu Gly Glu Pro Cys Gly Ile Val Met Ser Leu
            755                 760                 765
Pro Thr Ser Gly Thr Ala Val Val Asp Arg Leu Ala Asn Phe Gly Leu
    770                 775                 780
Pro Pro Ala Arg Ala Glu Leu Arg Glu Val Pro Phe Gly Gly Tyr Gln
785                 790                 795                 800
Arg Ser Val Thr Asn Thr Asn His Arg Val Lys Val Ser Val Ser Gly
                805                 810                 815
Gly Arg Ala Val Val Gln Lys Gly Asn Lys Ala Glu Met Asn Pro Val
            820                 825                 830
Phe Val Asn Arg Thr Pro Gly Gln Thr Thr Leu Gly Gln Pro Thr Thr
            835                 840                 845
Asp Thr Thr Gly Met Thr Thr Ala Asp Phe Leu Asp Ile
            850                 855                 860
```

PISCINE MYOCARDITIS VIRUS-LIKE PARTICLES AND METHODS OF USE THEREOF

CROSS REFERENCE TO RELATED APPLICATIONS

This application claims priority to GB 1701573.6, filed Jan. 31, 2017, all contents of which are incorporated by reference in their entirety.

FIELD OF THE INVENTION

The present invention relates to piscine myocarditis virus (PMCV) virus-like particles (VLP), and their use, for example as a medicament to treat or prevent cardiomyopathy syndrome (CMS) in fish.

BACKGROUND

CMS is an inflammatory heart disease, primarily affecting farmed Atlantic salmon, *Salmo salar* L. The disease was first detected in Norway in 1985 and has since been diagnosed in both farmed and wild Atlantic salmon.

CMS is most commonly diagnosed during the late seawater phase in farmed salmon and is a disease causing considerable losses for the salmon industry. The clinical features of CMS vary from acute death without prior clinical signs to elevated mortality with nonspecific signs such as impaired or abnormal swimming behaviour. Diagnosis of CMS is based on detection of characteristic inflammation and degeneration of spongy myocardium in the atrium and ventricle during histopathological examination.

The causative agent of CMS has been identified as piscine myocarditis virus (PMCV) and the isolation and characterisation of the virus is described in WO 2011/131600.

Methods of controlling the virus are urgently required but despite intensive research, it has not been possible to efficiently culture PMCV, or consequently to produce vaccines based on the attenuated or inactivated virus. Current approaches to vaccinating against CMS are, therefore, based on recombinant PMCV proteins, produced by recombinant expression systems in which no virus is used. Such vaccines, however, do not present the viral proteins in the natural structural context.

SUMMARY

In a first aspect, the present invention provides a recombinant piscine myocarditis virus (PMCV) virus-like particle (VLP) which consists only of PMCV ORF1 protein.

Preferably, the recombinant PMCV VLP consists only of PMCV ORF1 protein which has at least 70% sequence identity to the sequence set out in SEQ ID No: 2. In one embodiment the recombinant PMCV VLP consists only of PMCV ORF1 protein having between 70%-90% sequence identity to the sequence set out in SEQ ID No: 2. In one embodiment, the recombinant PMCV VLP consists only of PMCV ORF1 protein having at least 90% sequence identity to the sequence set out in SEQ ID No: 2.

Preferably, the recombinant PMCV VLP consists only of PMCV ORF1 protein which has a sequence which differs from the PMCV ORF1 protein sequence of SEQ ID No: 2 by no more than 80 amino acid residues. For example, the PMCV VLP may consist only of PMCV ORF1 protein which has a sequence which differs from the PMCV ORF1 protein sequence of SEQ ID No: 2 by no more than 15 amino acid residues.

In one or more embodiments the recombinant PMCV VLP may consist only of PMCV ORF1 protein having the sequence, or a fragment of the sequence, set out in SEQ ID No: 2.

In a second aspect, the present invention provides a method for the production of a recombinant PMCV VLP which consists only of PMCV ORF1 protein. The method comprises:
i) infecting an insect cell with a baculovirus expression vector encoding the PMCV ORF1 protein of the present invention; and,
ii) incubating the infected cell to allow the expression of PMCV ORF1 proteins for the production of a PMCV VLP.

Preferably, step i) infecting an insect cell with a baculovirus expression vector comprises incubating the cells at 27° C. for 24 hours.

Preferably, step ii) suitably incubating the infected cell comprises incubating the cell at a temperature in the range of 12-20° C. for a period of 2-10 days. For example, the cell may be incubated at a temperature in the range of 15-17° C. and/or for a period of 2-4 days.

In a third aspect, the invention provides a recombinant PMCV VLP which is obtained or obtainable by a method of the second aspect.

In a fourth aspect, the invention provides a recombinant PMCV VLP of the first aspect or the third aspect for use as a medicament. For example, the recombinant PMCV VLP may be suitable for use in treating or preventing cardiomyopathy syndrome (CMS) infections of fish.

In a fifth aspect, the present invention provides a vaccine comprising a recombinant PMCV VLP of the first aspect or third aspect for use in treating or preventing cardiomyopathy syndrome (CMS) infections in fish. In one embodiment the vaccine of the invention may further comprise at least one other antigen of a fish-pathogenic microorganism or a fish-pathogenic virus. In one embodiment the vaccine of the invention may comprise an adjuvant.

In a sixth aspect, the present invention provides a baculovirus expression vector comprising genetic information encoding the expression of PMCV ORF1 protein as defined in relation to the first aspect. For example, the baculovirus expression vector may comprise genetic information encoding only the expression of PMCV ORF1 protein as defined in relation to the first aspect.

In a seventh aspect, the present invention provides an insect cell comprising a baculovirus expression vector of the fourth aspect.

In an eighth aspect, the present invention provides the use of a baculovirus based expression system for the production of the PMCV VLP of the first aspect or third aspect.

In a ninth aspect, the invention provides a PMCV VLP substantially as described herein.

FIGURES

FIG. 1 shows the nucleotide sequence of the ORF1 of a specific isolate of PMCV, which corresponds to the sequence set out in SEQ ID No: 1.

FIG. 2 shows the amino acid sequence of the ORF1 of a specific isolate of PMCV, which corresponds to the sequence set out in SEQ ID No: 2, and which is encoded by the nucleotide sequence of SEQ ID No: 1 and FIG. 1.

DETAILED DESCRIPTION

Figure 3:
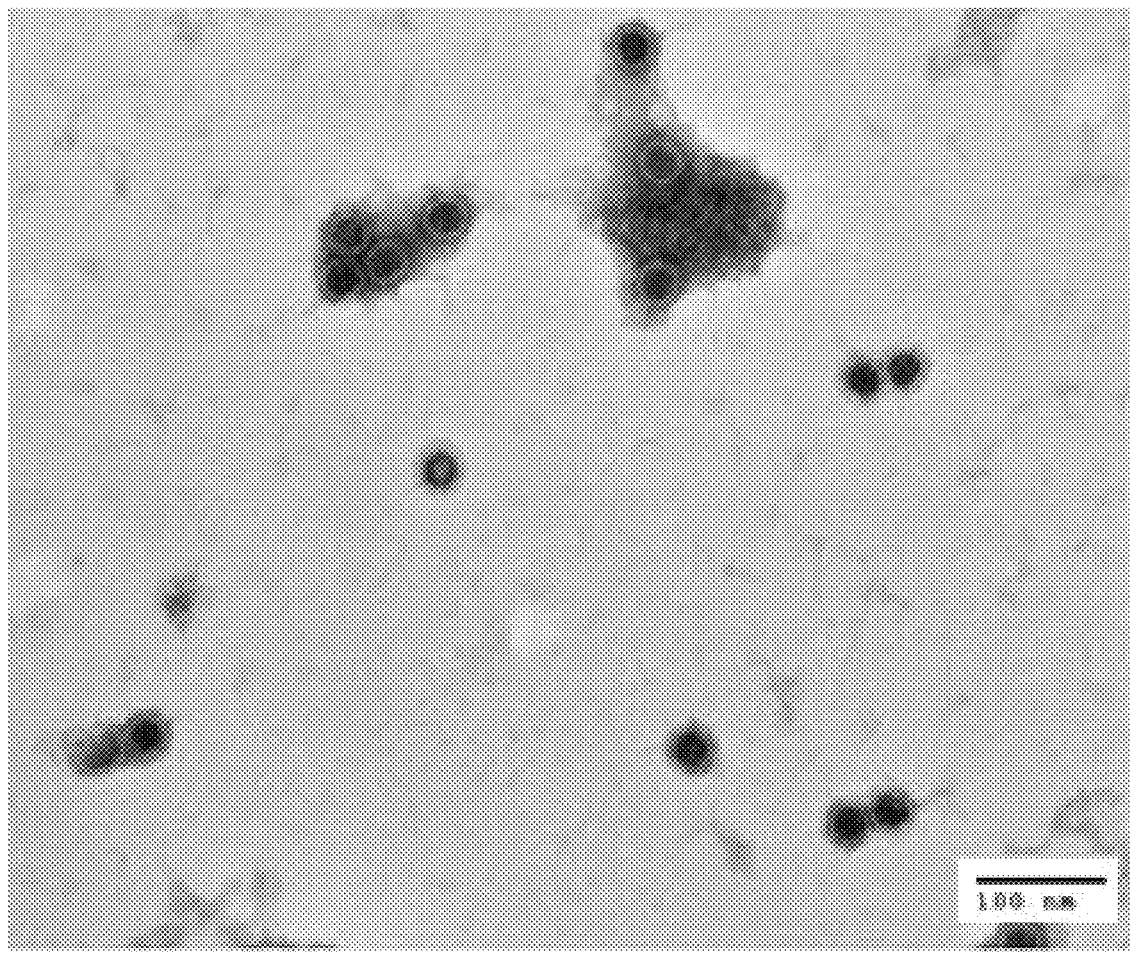
FIG. 3 is an electron micrograph showing PMCV virus-like particles produced in Tni cells expressing recombinant PMCV ORF1 protein only, as described in Example 6.
Figure 4:
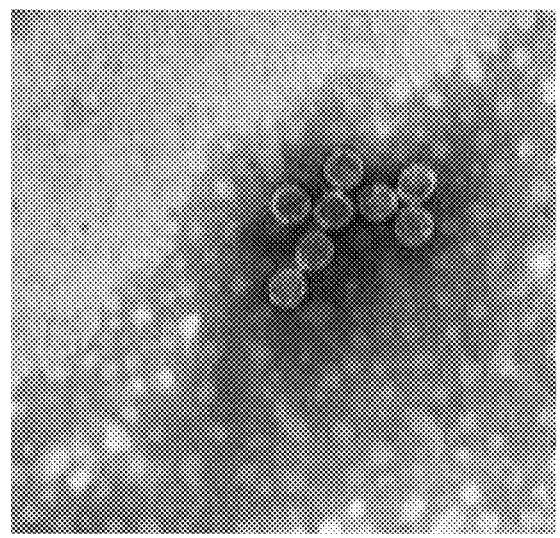
FIG. 4 is an electron micrograph showing PMCV virus-like particles produced in Tni cells expressing recombinant PMCV ORF1 and ORF3 proteins in combination, as described in Example 6.

PMCV is a double stranded RNA virus, with three open reading frames (ORF1, ORF2, and ORF3). PMCV has been classified in the family Totiviridae based on a low level of sequence identity between the PMCV ORF2 protein and an RNA-dependent RNA polymerase (RdRp) from Totiviridae. The other PMCV proteins, ORF1 and ORF3, however, have no significant homology to any other known proteins. The function of these proteins cannot be determined by homology to proteins from other Totiviridae due to the insufficient degree of sequence identity. Various other lines of evidence, however, have indicated that both ORF1 and ORF3 are coat proteins required for formation of the PMCV capsid. For example, in WO 2011/131600 both ORF1 and ORF3 are described as coat proteins. WO 2011/131600 also includes examples showing that antibodies that recognise the PMCV ORF1 or ORF3 proteins are capable of binding to intact CMS virus particles, indicating that at least a part of both the ORF1 and ORF3 proteins must be present on the surface of the virus.

Haugland et al (J Virol. 85 (11): 5275-5286), describe that PMCV is in many ways more similar to the putative totivirus Infectious Myonecrosis Virus (IMNV) of shrimp than other members of the family Totiviridae. For example, almost all other totiviruses asymptomatically and persistently infect fungi and protozoans and are transmitted to new host cells only during cell division, sporogenesis, and cell fusion. In contrast, both PMCV and IMNV can be transmitted extracellularly through the release of virus particles from infected cells, and both viruses cause myonecrosis in the host. The IMNV virions have fibre-like protrusions which are absent in other members of the family Totiviridae. The surface protrusions of IMNV are of a similar molecular weight and organisation to the PMCV ORF3 protein and in view of this, and the similarities in the modes of viral transmission, it is suggested that the ORF3 protein is a PMCV surface protein (Haugland et al).

The present application, however, is based on the surprising discovery that ORF3 is not required for the formation of the PMCV capsid and that PMCV virus-like particles can be made consisting only of ORF1 protein.

Virus-like particles are produced from viral coat proteins and structurally resemble the natural virion, and are, therefore, highly immunogenic, but contain no genetic material and are not infectious. To the inventors' knowledge, synthetic virus-like particles of any members of the family Totiviridae have not previously been produced, and for the first time, PMCV VLP, and methods of producing PMCV VLP, are now described in the present disclosure.

The genetic sequence of the PMCV ORF1 of the isolated PMCV described in WO 2011/131600 is given in SEQ ID No: 1. The corresponding protein sequence of the PMCV ORF1 is given in SEQ ID No. 2.

The protein sequence given in SEQ ID No. 2 is the protein sequence of one particular PMCV isolate, and as such is merely an example of a particular PMCV ORF1 protein. Due to genetic variation that inevitably exists between individual PMCV virus particles within the population as a whole, other PMCV ORF1 protein sequences also exist. For the purposes of the present invention, a PMCV ORF1 protein is considered to be any PMCV ORF1 protein encoded in the genome of any PMCV virus, which is transcribed from an open reading frame corresponding to the open reading frame designated for the purposes of the present invention (and conventionally in the PMCV field) as ORF1.

Thus, in some embodiments, the PMCV VLP may consist only of PMCV ORF1 protein having a protein sequence that is identical to, or substantially identical to, the sequence, or a fragment of the sequence, set out in SEQ ID No: 2. For the avoidance of doubt, the terms "substantially identical", "substantially similar" or "substantially the same" denotes a sufficiently high degree of similarity between two numeric values (such as one associated with the ORF1 protein sequence of a given PMCV and the other associated with the ORF1 protein sequence set out in SEQ ID No: 2) such that the skilled person would consider the difference between the two values to be of little or no biological and/or statistical significance within the context of the biological characteristic measured by said values (such as sequence identity). Unless otherwise stated, the difference between the two values is less than about 20%, 10%, 7%, 5%, or preferably less than about 3%, 2%, 1.5%, 1%, or 0.5% of the reference value.

However, the genome sequences of individual PMCV viruses in the population as a whole are not identical and, as a result, the sequences of PMCV ORF1 proteins within the population may differ. The skilled person would understand that a particular PMCV ORF1 protein may not necessarily have a protein sequence that is identical to, or substantially identical to, the sequence given in SEQ ID No: 2. Thus, in some embodiments, the PMCV VLP may consist only of a protein or fragment having a sequence which has at least 70% sequence identity to the PMCV ORF1 protein sequence set out in SEQ ID No: 2. For example, the PMCV VLP may consist only of a protein or fragment having a sequence which has at least 75%, 80%, 85%, 90%, 95%, or 97% sequence identity to the PMCV ORF1 protein sequence set out in SEQ ID No: 2. In preferred embodiments, the PMCV VLP consists of a protein or fragment having a sequence which has at least 97%, 97.5%, 98%, 98.5%, 99%, 99.5% sequence identity to the PMCV ORF1 protein sequence set out in SEQ ID No: 2.

The PMCV ORF1 protein of SEQ ID No: 2 has 861 amino acid residues in total. In some embodiments, the PMCV VLP of the invention consists only of a protein or fragment having a sequence which differs from the PMCV ORF1 protein sequence of SEQ ID No: 2 by no more than 80, 60, 50, 40, 30, or 20 amino acid residues. Preferably, the PMCV ORF1 protein sequence of the invention differs from that of SEQ ID No: 2 by no more than 15, 12, 10, 8, 7, 6, or 5 amino acid residues. Even more preferably, PMCV ORF1 protein sequence of the invention differs from the protein sequence of SEQ ID No: 2 by only 4, 3, 2, or 1 amino acid. In some embodiments the PMCV ORF1 protein sequence of the invention differs from the protein sequence of SEQ ID No: 2 by amino acid substitutions in one or more of the following specific positions (corresponding to the residue numbers of the sequence set out in SEQ ID No: 2): 37, 40, 57, 248, 300, 401, 442, 484, 486, 490, 587, 645, 655, 773, and/or 774. In some embodiments the PMCV ORF1 protein sequence of the invention differs from the protein sequence of SEQ ID No: 2 by one or more of the following specific amino acid substitutions: A to V at position 37, A to V at position 40, G to S at position 57, S to N at position 248, D to G at position 300, A to T at position 401, M to T at position 442, A to G at position 484, A to P at position 486, P to L at position 490, M to T at position 587, Y to H at position 645, H to R at position 655, T to A at position 773, and/or A to V at position 774.

The PMCV ORF1 nucleotide sequence of SEQ ID No: 1 has 2586 nucleotides in total. Due to the redundancy in the genetic code it would be possible to alter at least 800 nucleotides of the sequence of SEQ ID No: 1 without changing the identity of a single amino acid residue of the encoded amino acid sequence from that set out in SEQ ID No: 2. Thus, in some embodiments, the PMCV VLP of the invention consists only of a protein or fragment encoded by a sequence which differs from the PMCV ORF1 nucleotide sequence of SEQ ID No: 1 by no more than 1200, 1100, 1000, 950, 900, or 850 nucleotides. In some embodiments, the PMCV VLP may consist only of a protein or fragment encoded by a nucleotide sequence which has at least 70% sequence identity to the PMCV ORF1 nucleotide sequence set out in SEQ ID No: 1. For example, the PMCV VLP may consist only of a protein or fragment encoded by a nucleotide sequence which has at least 75%, 80%, 85%, 90%, 95%, 97%, or 99% sequence identity to the PMCV ORF1 nucleotide sequence set out in SEQ ID No: 1.

For the avoidance of doubt, the terms "% sequence identity", "% sequence similarity", "% identical", "% identity", "% homology", and similar terms, are to be understood to refer to the percentage of nucleotides or amino acid residues that two or more sequences or fragments, when optimally aligned, contain that are the same, after aligning the sequences and introducing gaps, if necessary, to achieve the maximum percent sequence identity, and not considering any conservative substitutions as part of the sequence identity. The skilled person will acknowledge that various means for comparing sequences are available. For example, one non-limiting example of a computer sequence alignment program is the Basic Local Alignment Search Tool (BLAST). Those skilled in the art can determine appropriate parameters for measuring alignment, including any algorithms needed to achieve maximal alignment over the full length of the sequences being compared. The % amino acid (or nucleotide) sequence identity of a given amino acid (or nucleotide) sequence A to, with, or against a given amino acid (or nucleotide) sequence B (which can alternatively be phrased as a given amino acid (or nucleotide) sequence A that has or comprises a certain % amino acid (or nucleotide) sequence identity to, with, or against a given amino acid (or nucleotide) sequence B) is calculated as [100 times the fraction X/Y] where X is the number of amino acid (or nucleotide) residues scored as identical matches in the alignment of A and B, and where Y is the total number of amino acid (or nucleotide) residues in B. It will be appreciated that where the length of amino acid (or nucleotide) sequence A is not equal to the length of amino acid (or nucleotide) sequence B, the % amino acid (or nucleotide) sequence identity of A to B will not equal the % amino acid (or nucleotide) sequence identity of B to A. A specified percentage of nucleotides or amino acid residues can be referred to as having, for example, 70%, 80%, 85%, 90%, 95%, 99% sequence identity or homology over a specified region when compared and aligned for maximum correspondence. Unless otherwise stated, the determination of sequence identity/homology is based on a comparison of the entire sequences, and not on selected portions.

In some embodiments, the PMCV VLP may consist only of PMCV ORF1 protein which is a fragment or variant of the protein sequence set out in SEQ ID No: 2, and/or which is encoded by a fragment or variant of the nucleotide sequence of SEQ ID No: 1. The term "variant" used in respect of the nucleic acid sequences and proteins according to the present invention is to be understood to encompass nucleic acid sequences and proteins that only differ from the reference sequences by way of amino acid or nucleotide additions, deletions, or alterations that have little or no effect on the functional activity of the claimed sequences. The skilled person will acknowledge that modifications of a protein sequence or protein coding nucleotide sequence may be introduced which do not alter, or do not significantly alter, the structure or properties of the folded protein. For example, the substitution of a nucleotide in a triplet codon may not alter the identity of the encoded amino acid. Similarly, alterations of the nucleic acid sequence resulting in modifications of the amino acid sequence of the corresponding recombinant protein may have little, if any, effect on the protein's ability to form VLP if the alteration does not have any impact on the resulting three dimensional protein structure. For example, a codon for a hydrophobic amino acid may be substituted by a codon encoding another hydrophobic residue. Similarly, changes which result in substitution of one negatively or positively charged residue for another can also be expected to produce little or no alteration in the resulting folded protein's tertiary structure or function. Therefore, references to "variants" of nucleic acid or protein sequences of the invention will be understood to encompass all such modifications which result in the production of a biologically equivalent protein.

The PMCV ORF1 protein of the invention must be functional in the sense that the PMCV ORF1 protein must be capable of forming part of a PMCV VLP. Regardless of the degree of sequence identity that a given protein has to the sequence set out in SEQ ID No: 2, the protein cannot be considered a PMCV ORF1 protein for the purposes of the invention if it cannot be used in the formation of a PMCV VLP. This clearly sets a functional limitation on the extent to which a PMCV ORF1 protein of the VLP of the invention may differ from the protein of SEQ ID No: 2; PMCV ORF1 proteins that are fragments or variants of the protein of SEQ ID No: 2 which are not capable of forming part of a PMCV VLP are not considered to be PMCV ORF1 proteins for the purposes of the present invention.

The PMCV VLP of the invention consists only of PMCV ORF1 protein. For the avoidance of doubt, the terms "consists of", "consisting of", and related terms, are intended to be interpreted in an exclusive manner Thus, the PMCV VLP of the invention is composed of multiple copies of PMCV ORF1 protein only. Specifically, the PMCV VLP does not include any other proteins that are not, or cannot be considered to be, PMCV ORF1 proteins, or indeed any other materials whatsoever. For example, the PMCV VLP does not contain any other PMCV proteins or nucleic acids, such as PMCV ORF3 (or ORF2) protein, and the PMCV VLP does not contain any exogenous proteins or nucleic acids, for example, derived from any part of the cell or expression system used in the production of the PMCV VLP. In addition, for the avoidance of doubt, the phrase "consists only of PMCV ORF1 protein" is to be understood to mean that the virus-like particle consists of a plurality of PMCV ORF1 proteins only, and, specifically, the "consists of" language is to be understood to reflect that the VLP is composed only of a plurality of PMCV ORF1 proteins and does not contain any other proteins or materials of any kind.

The PMCV VLP preferably consists of multiple copies of identical PMCV ORF1 proteins. In some embodiments, however, any given two of the PMCV ORF1 proteins of an individual PMCV VLP may differ. Thus, in some embodiments, the nucleic acid or protein sequences of any given two of the PMCV ORF1 proteins of an individual PMCV VLP may have at least 70% sequence identity. For example, the nucleic acid or protein sequences of any given two of the PMCV ORF1 proteins of an individual PMCV VLP may have at least 75%, 80%, 85%, 90%, 95%, 97%, or 99% sequence identity. Preferably, any given two of the PMCV ORF1 proteins of an individual PMCV VLP may differ by no more than 15, 12, 10, 8, 7, 6, or 5 amino acid residues. Even more preferably, any given two of the PMCV ORF1 proteins of an individual PMCV VLP may differ by only 4, 3, 2, or 1 amino acid.

In preferred embodiments, the PMCV VLP of the invention are immunogenic in fish, and can be defined and identified on the basis of their immunogenic properties. The term "immunogenic" refers to the property that, when administered to fish (preferably salmonids), optionally together with an effective amount of a suitable adjuvant, in an immunogenically effective amount, the VLP of the invention induce the production of PMCV-specific antibodies in the fish. For the avoidance of doubt, an "effective amount" refers to an amount effective, at dosages and for periods of time necessary under normal circumstances, to achieve the desired result.

Thus, in some embodiments, the PMCV VLP, when administered in an immunologically effective amount, optionally together with an effective amount of a suitable adjuvant, may be capable of inducing the production in fish of neutralizing antibodies against PMCV.

In some embodiments, the PMCV VLP of the invention may be identified by the ability to bind an antibody raised against the PMCV ORF1 protein as defined in SEQ ID No: 2, such as a recombinant PMCV ORF1 protein made by any suitable method. Thus, the binding affinity between an antibody raised against the PMCV ORF1 protein of SEQ ID No: 2 and the PMCV VLP of the invention may be at least 50% of the binding affinity between the same antibody and the PMCV ORF1 protein of SEQ ID No: 2. Preferably, the binding affinity of the antibody for the PMCV VLP of the invention is at least 60%, 65%, 70%, 75%, 80%, 85%, 90%, 95%, 97%, 99%, and may be 100%, of the binding affinity of the antibody for the PMCV ORF1 protein of SEQ ID No: 2. Methods for the production of suitable detection antibodies are known. For example, such neutralizing antibodies can be polyclonal, such as those produced in immunized rabbits. Alternatively, antibodies may be polyclonal, for example produced as a hybridoma with B cells from immunized mice.

Such an antibody may be an antibody raised in fish such as salmonids. Thus, in some embodiments, the PMCV VLP may be capable of eliciting an immune response in fish vaccinated with recombinant PMCV ORF1 protein.

For the avoidance of doubt, the "binding affinity" refers to the strength of the sum total of noncovalent interactions between a single binding site of a molecule (such as an antibody) and its binding partner. Unless otherwise stated, "binding affinity" in relation to the present invention refers to intrinsic binding affinity which reflects a 1:1 interaction between members of a binding pair. The affinity of a molecule X for its partner Y can generally be represented by the dissociation constant (Kd). A variety of methods of measuring binding affinity are known in the art, any of which can be used for the purposes of the present invention.

Medical Use

For the first time, PMCV VLP can be made. The PMCV VLP structurally mimic wild-type virus particles and, as a result, are immunologically comparable to inactivated whole viruses.

Thus, the PMCV VLP of the invention may be suitable for use, or formulated for use, in or as a medicament. For the avoidance of doubt, a "medicament" is an agent or composition that is active to treat or prevent the disorder in question or its symptoms, or side effects. As used herein, "treatment" refers to clinical intervention in an attempt to alter the natural course of the individual being treated, and can be performed either for prophylaxis or during the course of disease. Desirable effects of treatment may, for example, include preventing occurrence or recurrence of disease, alleviation of symptoms, diminishment of any direct or indirect pathological consequences of the disease, decreasing the rate of disease progression, amelioration or palliation of the disease state, and/or remission or improved prognosis.

In some embodiments the PMCV VLP is suitable for use in treating or preventing viral infections of fish. In some embodiments the PMCV VLP is suitable for use in treating or preventing cardiomyopathy syndrome infections of fish, including salmonid fish.

Vaccine

The PMCV VLP of the invention may be used in the production of a vaccine. For the avoidance of doubt, the term "vaccine" refers to a material or composition that can produce an immune response that blocks the infectivity, either partially or fully, of an infectious agent, which in respect of the present invention is the virus PMCV which causes CMS, affecting fish such as Atlantic salmon. Thus, when the vaccines of the invention, comprising PMCV VLP consisting only of PMCV ORF1 protein, are administered to a fish, the fish is immunised against CMS caused by PMCV. A vaccine comprising the PMCV VLP of the invention may be formulated using known techniques. Preferably vaccines comprising the PMCV VLP of the invention may also comprise an effective amount of a suitable adjuvant.

Thus, another embodiment relates to a vaccine for the treatment or prevention of CMS infection of salmonid fish. The vaccine comprises the PMCV VLP of the invention. The vaccine may further comprise an effective amount of a suitable adjuvant.

Generally, the PMCV VLP of the invention may be formulated and used in a vaccine or other medicinal composition in ways and by means exactly the same as those known to the skilled person in relation to other immunogenic virus particles, including attenuated or inactivated viruses, and other VLPs.

For example, the vaccine may further comprise other additives that are used in the art for the production of such compositions, such as a carrier, a diluent, an adjuvant, a stabilizer, an emulsifier, or other agent, as described below.

Carriers

In some embodiments, the vaccine further comprises a pharmaceutically acceptable carrier and/or diluent. Examples of pharmaceutically acceptable carriers or diluents useful in the present invention include sterile water, saline, aqueous buffers such as PBS and others, culture medium, carbohydrates (such as sorbitol, mannitol, starch, sucrose, glucose, dextran), proteins (such as albumin or casein), protein containing agents such as bovine serum or skimmed milk, and buffers (such as phosphate buffer).

Adjuvants

In some embodiments, the vaccine further comprises an adjuvant. Adjuvants are non-specific stimulators of the immune system. They enhance the immune response of the host to the vaccine. Examples of suitable adjuvants known in the art include lipopolysaccharide, CpG, Freunds Complete and Incomplete adjuvant, vitamin E, non-ionic block polymers, muramyldipeptides, ISCOMs (immune stimulating complexes), Saponins, mineral oil, vegetable oil, and Carbopol. Oil adjuvants suitable for use in water-in-oil emulsions include, for example, mineral oils or metabolisable oils. Mineral oils include, for example, Bayol®, Marcol®, and Drakeol®. An example of a non-mineral oil adjuvant is Montanide-ISA-763-A. Metabolisable oils include, for example, vegetable oils, such as peanut oil and soybean oil, animal oils such as the oils squalane and squalene from shark liver or plants, and tocopherol and its derivatives.

Stabilisers

In some embodiments, the vaccine further comprises a stabiliser. A stabilizer can be added to the vaccine, for example, to protect it from degradation, to enhance the shelf-life, or to improve freeze-drying efficiency. Useful stabilizers include SPGA, skimmed milk, gelatine, bovine serum albumin, formalin, carbohydrates (such as sorbitol, mannitol, trehalose, starch, sucrose, dextran or glucose), proteins (such as albumin or casein or degradation products thereof), and buffers, such as alkali metal phosphates.

Emulsifiers

In some embodiments, vaccines comprising the PMCV VLP of the invention further comprise one or more suitable surface-active compounds or emulsifiers, such as Span®, Cremophore®, or Tween®.

Form of Vaccine

Vaccines comprising the PMCV VLP of the invention may be prepared in any suitable form, including forms generally used for the production and preparation of viral vaccines. For example, the vaccine of the invention may be in the form of an emulsion, a suspension, in a lyophilized form or, alternatively, in a frozen form. If the formulation is to be frozen, glycerol or other similar agents may be included in the formulation to enhance the stability of the VLP when frozen. Reconstitution is advantageously effected in sterile water or a suitable buffer.

Fish

Vaccines comprising the PMCV VLP of the invention are preferably administered to fish, which may, for example, be any species of fish that is susceptible to CMS infection. Of particular note, the vaccine is suitable for administration to, and for treating, a fin fish, which may be a telostei, for example, of the order Salmoniformes. Preferably, the claimed formulation may be used to treat salmon such as Atlantic and Pacific salmon, such as Coho salmon, arctic char, and trout such as rainbow trout and brown trout.

Route of Administration

The present invention includes methods of vaccinating fish against CMS infection. Methods comprise administering to a fish a vaccine composition comprising the PMCV VLP of the invention, optionally together with a suitable adjuvant.

The vaccine composition may be administered to the host in any suitable manner known in the art. In particular, vaccine formulations comprising the PMCV VLP of the invention may be suitable for parenteral administration, such as by intraperitoneal injection. Other conventional fish vaccination methods may also be used if appropriate, including immersion, dipping, or oral administration.

Dosage

Vaccines comprising the PMCV VLP of the invention are preferably used, optionally together with a suitable adjuvant, in immunologically-effective amounts. For the avoidance of doubt, in this context, the expression "immunologically-effective amount" means the amount of PMCV VLP, optionally together with an adjuvant, that is required to stimulate the production of protective levels of immunity in a host. Thus, the PMCV VLP of the invention is used in an amount, or in a composition, that is sufficient to induce an immune response in fish that decreases the pathological effects caused by infection with a wild-type PMCV, in comparison to the pathological effects caused by infection with a wild-type PMCV in non-immunized fish.

The dosage of the vaccine (and the route of administration) employed will be dependent on various factors including the size and weight of the host, the vaccine formulation (such the presence of an adjuvant), and the timing of the administration. Generally, dosages may need to be increased for larger, more robust fish, and decreased for smaller, more delicate fish.

Vaccines comprising the PMCV VLP of the invention can generally be administered by injection in a dosage of $10^3$ to $10^{12}$ VLP, such as $10^4$ to $10^{11}$ VLP, $10^5$ to $10^{10}$ VLP, or $10^6$ to $10^{10}$ VLP. Preferably the dosage contains in the range of $10^7$ to $10^9$ VLP more preferably between $10^8$ and $10^9$ VLP per dose.

Combination Vaccines

In some embodiments, vaccines comprising the PMCV VLP of the invention are combination vaccines and further comprise an immunologically-effective amount of at least one additional immunogenic agent. Thus, another embodiment relates to a vaccine for the treatment or prevention of CMS infection and one or more other infections of fish. The vaccine comprises the PMCV VLP of the invention together with an immunogenic amount of at least one other antigen against a fish-pathogenic microorganism or a fish-pathogenic virus.

The at least one other vaccine may comprise an antigen from a bacterial source, a viral source, a parasitical source, and/or a fungal source. Polyvalent vaccines containing antigens from typical fish pathogens are well known in the art and are already commercially available.

The antigen from a bacterial source may be selected from the group comprising: live, attenuated or killed bacteria of the species *Piscirickettsias* sp. *Aeromonas* sp., *Vibrio* sp., *Listonella* sp., *Moritella viscosa, Photobacterium damsela, Flavobacterium* sp., *Yersinia* sp., *Renibacterium* sp., *Streptococcus* sp., *Lactococcus* sp., *Leuconostoc* sp., *Bifidobacterium* sp., *Pediococcus* sp., *Brevibacterium* sp., *Edwarsiella* sp., *Francisella* sp., *Pseudomonas* sp., *Cytophaga* sp., *Nocardia* sp., and *Mycobacerium* sp.

The antigen from a viral source may be selected from the group comprising:

Viral Hemorrhagic Septicemia Virus (VHSV), Infectious Hematopoietic Necrosis virus (IHNV), Infectious Pancreatic Necrosis Virus (IPNV), Spring Viremia of Carp (SVC), Channel Catfish Virus (CCV), Infectious Salmon Anaemia virus (ISAV), pancreatic disease virus (SPDV), Iridovirus, and piscine orthoreovirus (PRV).

The antigen from a parasitic source may be selected from the group comprising: *Lepeophtheirus* Sp., *Caligus* Sp., and *Ichthyophthirius* Sp.

The antigen from a parasitic source may be selected from the group comprising: *Saprolegnia* Sp., *Branchiomyces sanguinis, Branchiomyces demigrans* and *Icthyophonus hoferi*.

Method of Manufacture

The PMCV VLP of the invention may be manufactured by any suitable method. In preferred embodiments the PMCV VLP of the invention are made in a baculovirus based expression system.

Baculovirus expression systems used in conjunction with insect cells have become well-established for the production of proteins. In such systems, a recombinant baculoviral vector is used to introduce the gene of interest (in this case PMCV ORF1) into insect cells under the control of a strong baculoviral promoter. Infection of the insect cells in this way results in replication of the recombinant baculovirus vector genome, thereby increasing the number of genetic templates that encode the gene of interest and increasing the level of recombinant protein expression. Baculovirus-mediated protein expression also provides correct folding of recombinant proteins and other important post-translational modifications that provide proper biological activity and function to the expressed proteins. The insect cells used in the system can be grown on serum free media which may have further advantages in terms of costs and biosafety.

Thus, in some embodiments, the invention relates to a baculovirus expression vector comprising the PMCV ORF1 gene, which is defined for the purposes of the present invention as all of the genetic information encoding the expression of a PMCV ORF1 protein. In preferred embodiments the genetic information encodes the expression of a PMCV ORF1 protein only. Thus, the invention also relates to a baculovirus expression vector comprising a polynucleotide encoding at least PMCV ORF1 protein, such as PMCV ORF1 protein only.

For example, the invention also relates to a baculovirus expression vector comprising the nucleotide sequence of SEQ ID No: 1. In some embodiments, the invention relates to a baculovirus expression vector comprising a nucleotide sequence encoding a PMCV ORF1 protein as described above, which is capable of forming a PMCV VLP.

The invention also relates to the use of a baculovirus based expression system for the production of PMCV VLP consisting only of PMCV ORF1 protein.

The invention also relates to a method for the production of PMCV VLP in a baculovirus based expression system, comprising the steps of:
a) infecting an insect cell line with a baculovirus expression vector encoding the expression of PMCV ORF1 protein; and,
b) suitably incubating the infected cells to allow the expression of the PMCV ORF1 protein and the production of the PMCV VLPs.

The invention also relates to a method for the production of an immunogenic composition comprising PMCV VLP. Optionally the method comprises steps a) and b) above and further comprises the step of preparing an immunogenic composition comprising the PMCV VLP.

Cells

Any suitable cell line may be used for the production of the PMCV VLP. The cells preferably used for the expression of PMCV ORF1 and production of the VLPs are cells that are suitable for use in a baculovirus expression system. Preferred cell lines include Sf21 cells (originally derived from the pupal ovarian cells of *Spodoptera frugiperda*), Sf9 cells (which are a clonal isolate of Sf21), and Tni (also called *T. ni* or TnHi5™) cells (which are originally derived from the ovarian cells of *Trichoplusia ni* (cabbage looper).

PMCV ORF1 protein has surprisingly been found to be expressed in significantly greater quantities in Tni cells than in other cell types, and thus Tni are the preferred cell type for use in the invention.

Baculovirus Expression System

There are a number of commercial systems available for expressing recombinant proteins using baculovirus, including flashBAC™ (Oxford Expression Technologies EP 1 144 666), BackPack™ (BD Biosciences Clontech), BacVector® 1000/2000/3000 (Novagen®). BAC-TO-BAC® (Invitrogen™), and BaculoDirect™ (Invitrogen™). All of these systems are based on the principle of expressing recombinant proteins by placing them under the control of the very late baculovirus promoters polh or p10. In preferred embodiments of the invention the PMCV VLP are produced using the flashBAC™ system.

Infection

Cells to be infected with the baculovirus expression vector encoding the expression of PMCV ORF1 protein may be cultured at a density of about $1 \times 10^4$-$1 \times 10^8$ cells/ml, such as $1 \times 10^5$-$1 \times 10^7$ cells/ml, and preferably the cells are cultured at a density of about $1 \times 10^6$ cells/ml.

The vector is added to the cells at a multiplicity of infection (MOI) of about 0.5-5, such as about 1-3, or preferably about 2. For the avoidance of doubt, the MOI is defined for the purposes of the present invention as the ratio of agents (in this case baculovirus expression vectors) to infection targets (in this case cells of a suitable insect cell line). Following addition of the vector to the cell culture, the cells are preferably incubated at a temperature of 25-29° C., such as at or about 26° C., 27° C., or 28° C. The cells are preferably incubated at this temperature for a period of about 12-36 hours, such as about 18, 21, 24, 27, or 30 hours.

Incubation

Incubating the infected cells to allow the expression of the PMCV ORF1 protein and the production of the PMCV VLPs generally involves incubating the cells for at least 1, 2, or 3 days and up to about 4, 5, 6, 8, or 10 days. Preferably, the cells are incubated for about 1-6 days, and most preferably about 2-4 days.

Baculovirus expression systems are always used at or close to 26-28° C. because that is the optimal temperature for both the infection process and the expression process. The use of this temperature is consistent with both the manufacturer's instructions, and the fact that the system would be expect to optimised to the host body temperature.

However, as detailed in the following Examples, it has surprisingly been found that if this temperature is used to incubate the cells infected with a baculovirus expression vector comprising PMCV ORF1, the protein is produced in significant quantities but does not form PMCV VLP.

In IMNV and other totiviruses that are capable of infecting new host cells, the proteins are translated as a precursor protein which is then proteolytically cleaved. However, PMCV ORF1 is not processed in any way, and in particular, does not require proteolytic cleavage or any other post-translational modification in order to form the mature PMCV ORF1 protein. It was, therefore, extremely unexpected to observe production of the PMCV ORF1 protein but no VLP. It has now surprisingly been found, however, that PMCV VLP can be produced if the incubation temperature used to allow the expression of the PMCV ORF1 protein and the production of the PMCV VLP is significantly below the temperature prescribed by the manufacturers of the expression system and used conventionally in the art.

Thus, in preferred embodiments, the incubation step of the method comprises incubating the cells at a temperature in the range of 12-20° C., such as 14-18° C., and preferred incubation temperatures are 15, 16, or 17° C.

Preparing a PMCV VLP Composition

Optionally the method for the production of PMCV VLP in a baculovirus based expression system includes a final step of isolating the PMCV VLPs from the culture medium. Suitable methods of isolating/purifying the VLP from the cell culture will be known to the skilled person and any suitable method may be used.

The isolation may be comprehensive, to provide essentially purified PMCV VLP, or may be less comprehensive, for example, involving simply the removal of cell debris and remaining baculoviruses such as by a suitable filtration method.

In some embodiments, the VLP are not isolated to any extent from the cell culture prior to the production of a vaccine or other medicinal composition. In such embodiments, further non-isolating treatment of the cell culture may nevertheless be used, such as formalin or heat treatment of the cultures or a treatment to lyse the cells.

EXAMPLES

The invention will now be explained in further detail in the following Examples, which demonstrate the development of the claimed PMCV VLP, consisting only of PMCV ORF1 protein.

Example 1. Production of Recombinant Baculoviruses

Recombinant baculoviruses were constructed using the flashBAC system from Oxford Expression Technologies following the manufacturer's instructions. PMCV ORF1 and PMCV ORF3 genes with an added His-tag were cloned into the transfer vector.

Recombinant baculoviruses were produced by co-transfection of Sf9 insect cells with duplicate reaction mixtures, each containing flashBACUltra viral DNA (100 ng) and transfer vector DNA (500 ng) for ORF1 or ORF3, together with Lipofectin liposome forming reagent (Invitrogen).

The mix was added to 35 mm² dishes with Sf9 insect cells seeded at a density of $1 \times 10^6$ cells/dish. The dishes were then incubated at 28° C. for 5 days, following which the medium containing each virus was harvested into sterile tubes.

Stocks of the recombinant PMCV ORF1 and PMCV ORF3 baculoviruses were then made, and titres determined, following the manufacturer's instructions.

Example 2. Protein Expression

Sf9 cells were seeded in 35 mm² dishes at $1 \times 10^6$ cells/dish, and Tni cells were seeded at $0.5 \times 10^6$ cells/dish. Each dish was infected with the virus (MOI=5).

Following incubation for 72 hrs at 28° C. the cell pellets and supernatants were harvested from each dish and run on a pre-cast 4-16% NuSep LongLife SDS-PAGE gel (Generon) with Fermentas PageRuler Prestained protein ladder Plus. Negative control was also included. Western blots were prepared using anti-His antibody at a dilution of 1:1000. Visualisation was by anti-mouse antibody: alkaline phosphatase conjugate (1:30,000 dilution) using detection reagents NBT and BCIP. The size (mass) of the ORF1 protein was approximately 100 kDa, and the size (mass) of the ORF3 protein was slightly greater than 35 kDa.

Both Sf9 and Tni cells were found to express both ORF1 and ORF3 protein, but Tni cells expressed the proteins in much greater quantities than Sf9 cells.

Example 3. Protein Expression

Expression experiments were carried out by infecting 20 ml cultures of Tni cells (at $1 \times 10^6$ cells/ml) at MOI=2 with the ORF1, ORF3, or a combination of the ORF1 and ORF3, recombinant baculoviruses.

The cells were incubated at 28° C. until 96 hours post-infection (hpi). The cell pellets were spun down at 4,000 rpm for 15 minutes and the pellet resuspended in 10 ml PBS. The resuspended pellets were lysed by freeze thawing, and the samples were centrifuged at 4,000 rpm for 30 minutes to remove cell debris. The supernatants were analysed by Western blot. The results are shown in Table 1, in which "+" indicates that a protein band was observed on the Western blot, and "-" indicates that no protein band was observed.

TABLE 1

| Expressed | Detection on Western blot | |
|---|---|---|
| Protein(s) | ORF1 (100 kDa) | ORF3 (35 kDa) |
| ORF1 | + | − |
| ORF3 | − | + |
| ORF 1 + ORF3 | + | + |

Results: This experiment shows that both ORF1 and ORF3 were expressed well in Tni cells using a baculovirus system.

Example 4. Detection of VLPs

Particles of the size expected for PMCV VLPs are pelleted by centrifugation at ~100,000 g. Thus, any PMCV proteins contained within virus-like particles will be observed on the Western blot in the pellet fraction produced under these centrifugation conditions.

Supernatants produced as described in Example 3 were centrifuged at ~100,000×g for 30 minutes to pellet any virus like particles. The resulting supernatants and pellets were analysed by Western blot.

The results are shown in Table 2, in which "+" indicates that a protein band was observed on the Western blot, and "-" indicates that no protein band was observed.

TABLE 2

| | Band detected on Western blot Fraction | | | |
|---|---|---|---|---|
| | Supernatant | | Pellet | |
| Protein(s) expressed | 100 kd (ORF1) | 35 kD (ORF3) | 100 kD (ORF1) | 35 kD (ORF3) |
| ORF1 | + | − | − | − |
| ORF3 | − | + | − | − |
| ORF 1 + ORF3 | + | + | − | − |

Results: Both ORF1 and ORF3 proteins were expressed in significant levels as soluble proteins in the cell culture and detected in significant quantities in the supernatant fraction. However, neither ORF1 nor ORF3 proteins were detected in the pellet fraction. Thus, although ORF1 and ORF3 proteins were observed to be expressed in significant quantities, no virus-like particles were formed. This was the case when ORF1 and ORF3 proteins were expressed individually or in combination.

Example 5. Protein Expression and Detection of VLP

The ORF1 and ORF3 proteins were found to be expressed efficiently under the incubation conditions conventionally used and in accordance with the manufacturer's instructions, but despite the significant expression of the ORF1 and ORF3 proteins, no PMCV VLP were observed to be formed.

To determine whether the expressed PMCV ORF1 and/or ORF3 proteins could be induced to form VLP, the protein expression experiments were repeated in which different variables of the incubation conditions were investigated, including the MOI, the incubation time, and the incubation temperature.

The expression experiments were carried out by infecting 20 ml cultures of Tni cells ($1\times10^6$ cells/ml) at MOI=2 with the ORF1, ORF3, or a combination of the ORF1 and ORF3, recombinant baculoviruses.

Adjusting different experimental parameters and conditions, including the MOI and the incubation time, did not result in the production of significant quantities of PMCV VLP.

To investigate the effect of incubation temperature on the production of PMCV VLP, cells were infected by incubation at 28° C. for 24 hrs before being incubated at 15° C. until 120 hpi. The cells were harvested and pelleted by centrifugation at 4,000 rpm for 15 minutes and the washed pellets were resuspended in 10 ml PBS. The resuspended pellets were lysed by freeze thawing, and the samples were centrifuged at 4,000 rpm for 30 minutes to remove cell debris. The supernatants were collected and centrifuged at ~100,000 g for 30 minutes to pellet any virus like particles.

The resulting pellets were resuspended in 0.5 ml PBS and used for both western blot and electron microscopy analysis (see below). The supernatants were also analysed by Western blot (described in Example 6). The results are shown in Table 3, in which "+" indicates that a protein band was observed on the Western blot, and "-" indicates that no protein band was observed.

TABLE 3

| | Detection on Western blot Fraction | | | |
|---|---|---|---|---|
| | Supernatant | | Pellet | |
| Expressed Protein(s) | ORF1 (100 kDa) | ORF3 (35 kDa) | ORF1 (100 kDa) | ORF3 (35 kDa) |
| ORF1 | − | − | + | − |
| ORF3 | − | + | − | − |
| ORF 1 + ORF3 | − | + | + | − |

Results: When PMCV ORF3 protein only was expressed, by incubating the infected cells at 15° C., no virus like particles were found to be formed. After centrifugation of the cell lysates at ~100,000 g for 30 minutes ORF3 protein was detected in the supernatant fraction only and not in the pellet fraction.

When both PMCV ORF1 and ORF3 proteins were expressed simultaneously, by incubating the infected cells at 15° C., virus-like particles were formed, but surprisingly the virus-like particles were found by Western blot to be composed solely of ORF1 protein, and in particular, ORF3 protein was not detected in the pellet fraction by Western blot. Thus, although ORF1 and ORF3 proteins were expressed in significant levels in the cells, the PMCV VLP produced contained ORF1 protein only and no ORF3 protein.

When PMCV ORF1 protein only was expressed, by incubating the infected cells at 15° C., virus like particles were found to be produced. The virus like particles were found by Western blot to contain ORF1 protein. Moreover, the formation of the virus like particles consisting only of PMCV ORF1 protein was found to be highly efficient because very little ORF1 protein was detected in the supernatant fraction. Thus, substantially all of the ORF1 protein that was expressed in the cells was found to be incorporated into virus like particles.

Each of the pellet fractions produced by centrifuging the cell lysates at 100,000 g for 30 minutes was also analysed by electron microscopy (see Example 6).

Example 6. Electron Microscopy

The re-suspended pellet fractions described in Example 5 were processed for electron microscopy. Samples were applied to Formvar and carbon-coated grids and adsorbed alone for 5 minutes and then with five droplets of 2% ammonium molybdate. Excess liquid was wicked away and the samples were air dried. The grids were examined with a Hitachi H7650 transmission electron microscope.

An example of one of the images obtained by electron microscopy of the pellet fraction of a sample in which PMCV ORF1 protein only was expressed at 15° C., as described above (in Example 5), is shown in FIG. 1. FIG. 2 shows an example image obtained by electron microscopy of the sample produced by the expression of ORF1 and ORF3 proteins in combination.

The electron microscopy images of FIGS. 1 and 2 show round structures with a diameter of about 30-40 nanometres. These structures are exactly as expected for empty PMCV particles both in predicted shape and size.

No virus-like particles were observed in the pellet fraction of samples in which PMCV ORF3 protein only was expressed.

Example 7. Vaccine Containing PMCV VLP Antigen

Antigen was produced by infecting 20 ml cultures of Tni cells ($1\times10^6$ cells/ml) at MOI=2 with the ORF1, ORF3, or a combination of the ORF1 and ORF3, recombinant baculoviruses.

The cells were incubated at 28° C. for 24 hrs before being placed at 15° C. until 120 hpi, as described above in Example 4. The Tni cells were spun down at 4,000 rpm for 15 minutes and the cell pellets were re-suspended in 10 ml PBS. The re-suspended pellets were lysed by freeze thawing, and samples were centrifuged at 4,000 rpm for 30 minutes to remove cell debris. The supernatants were harvested, and the amount of VLP quantified by Western blot. Remaining baculoviruses were inactivated by the addition of formalin.

Vaccines were formulated as a water-in-oil emulsion using standard techniques.

Example 8. Vaccination and Challenge Trial

Atlantic salmon post smolts (weighing about 30 g each) were injected with vaccine comprising PMCV VLP prepared as described above (in Example 7).

Six weeks post vaccination the fish were challenged intramuscularly with a preparation comprising homogenised heart tissue from fish diagnosed with severe CMS.

At 7 weeks post challenge, changes in the ventricle of the hearts of the vaccinated fish was determined by histological analyses using standard methods.

Results:

|  | Score 1 | Score 2 | Score 3 |
|---|---|---|---|
| VLP vaccine | 100% | — | — |
| Control vaccine (with irrelevant antigens) | 60% | 40% | — |

The results show that no fish vaccinated with VLP vaccine had severe pathology in the heart ventricle, while 40% of the fish vaccinated with a control vaccine had severe pathology in the heart ventricle. This shows that a vaccine using ORF1 VLP as antigen can protect salmon against severe pathology in the heart ventricle.

In order to address various issues and advance the art, the entirety of this disclosure shows by way of illustration various embodiments in which the claimed invention may be practiced and provide an PMCV VLP consisting only of PMCV ORF1 protein. The advantages and features of the disclosure are of a representative sample of embodiments only, and are not exhaustive and/or exclusive. They are presented only to assist in understanding and teach the claimed features. It is to be understood that advantages, embodiments, examples, functions, features, and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist essentially of, various combinations of the disclosed elements, components, features, parts, steps, means, etc. In addition, the disclosure includes other inventions not presently claimed, but which may be claimed in future.

The invention claimed is:

1. A recombinant piscine myocarditis virus (PMCV) virus-like particle (VLP) comprising a PMCV ORF1 protein, having at least about 90% sequence identity to the sequence comprising SEQ ID No: 2.

2. The recombinant PMCV VLP of claim 1, comprising the PMCV ORF1 protein having at least about 95% sequence identity to the sequence comprising SEQ ID No: 2.

3. The recombinant PMCV VLP of claim 2, comprising the PMCV ORF1 protein having at least about 99% sequence identity to the sequence comprising SEQ ID No: 2.

4. The recombinant PMCV VLP of claim 1, comprising the PMCV ORF1 protein having a sequence differing from the PMCV ORF1 protein sequence comprising SEQ ID No: 2 by no more than 80 amino acid residues.

5. The recombinant PMCV VLP of claim 4, comprising the PMCV ORF1 protein having a sequence differing from the PMCV ORF1 protein sequence of SEQ ID No: 2 by no more than 15 amino acid residues.

6. A method for the production of a recombinant PMCV VLP comprising the PMCV ORF1 protein of claim 1, the method comprising: a) infecting an insect cell with a baculovirus expression vector encoding the recombinant PMCV ORF1 protein of claim 2; and, b) incubating the infected cell of step (a) at a temperature in the range of 12-20° C. to allow the expression of the PMCV ORF1 protein in order to produce a PMCV VLP.

7. The method as in claim 6, wherein the incubation of the infected cell comprises incubating the cell at a temperature for a period of 1-10 days.

8. The method as in claim 7, wherein the incubation of the infected cell comprises incubating the cell at a temperature in the range of 15-17° C.

9. A PMCV VLP obtained by the method of claim 6.

10. A method of prevention of cardiomyopathy syndrome (CMS) infections in fish, the method comprising administering to the fish in need thereof the PMCV VLP according to claim 1.

11. A vaccine comprising the PMCV VLP of claim 10.

12. The vaccine of claim 11 further comprising at least one other antigen of a fish-pathogenic microorganism or a fish-pathogenic virus.

13. A baculovirus expression vector comprising the PMCV ORF1 protein as defined in claim 1.

14. An insect cell comprising a baculovirus expression vector of claim 13.

\* \* \* \* \*